United States Patent
Golz-Berner et al.

(10) Patent No.: US 6,309,627 B1
(45) Date of Patent: Oct. 30, 2001

(54) COSMETIC COMPOSITIONS WITH AGGLOMERATED SUBSTRATES

(75) Inventors: Karin Golz-Berner; Leonhard Zastrow, both of Monaco (DE)

(73) Assignee: Lancaster Group GmbH, Mainz (DE)

( * ) Notice: Subject to any disclaimer, the term of this patent is extended or adjusted under 35 U.S.C. 154(b) by 0 days.

(21) Appl. No.: 09/463,878

(22) PCT Filed: Jul. 21, 1998

(86) PCT No.: PCT/DE98/02087

§ 371 Date: Jan. 31, 2000

§ 102(e) Date: Jan. 31, 2000

(87) PCT Pub. No.: WO99/06012

PCT Pub. Date: Feb. 11, 1999

(30) Foreign Application Priority Data

Aug. 1, 1997 (DE) .............................. 197 34 547

(51) Int. Cl.⁷ ...................................... A61K 7/42
(52) U.S. Cl. .................... 424/59; 424/401; 424/709; 424/489
(58) Field of Search .............. 424/59, 709, 401, 424/489

(56) References Cited

U.S. PATENT DOCUMENTS

| | | | |
|---|---|---|---|
| 5,082,660 | 1/1992 | Hovic et al. | 424/63 |
| 5,234,682 | 8/1993 | Macchio et al. | 424/69 |
| 5,629,185 | 5/1997 | Stanzl et al. | 435/173.7 |
| 5,637,318 | 6/1997 | Gross et al. | 424/450 |
| 5,800,835 | 9/1998 | Zastrow et al. | 424/647 |
| 5,846,310 | * 12/1998 | Noguchi et al. | 106/482 |

FOREIGN PATENT DOCUMENTS

| | | |
|---|---|---|
| 36 16 133 | 11/1987 | (DE) . |
| 0 406 657 | 1/1991 | (EP) . |
| 0 433 086 | 6/1991 | (EP) . |
| 0 704 502 | 4/1996 | (EP) . |
| 08-104512 | 4/1996 | (JP) . |
| 08-217637 | 8/1996 | (JP) . |
| WO95/09895 | 4/1995 | (WO) . |
| WO96/17588 | 6/1996 | (WO) . |

* cited by examiner

Primary Examiner—Jos'e G. Dees
Assistant Examiner—Konata M George
(74) Attorney, Agent, or Firm—Collard & Roe, P.C.

(57) ABSTRACT

The invention relates to cosmetic compositions containing agglomerates with particular particle sizes. The compositions are characterized in that they contain spherical non-porous SiO2 particles with a particle size of 0.05–1.5 μm, and other inorganic particle-shaped materials with spherical structure. The spherical $SiO_2$ and other inorganic materials form defined agglomerates with a particle size of 0.06 μm to 5 μm. The proportion of agglomerates in the cosmetic composition is between 0.1 and 30% wt. The aggregate-containing dispersions are produced by introducing the spherical $SiO_2$ step by step and in special conditions. Formulations produced with these aggregates are characterized by particularly stable and high sunscreen factors.

11 Claims, No Drawings

COSMETIC COMPOSITIONS WITH AGGLOMERATED SUBSTRATES

BACKGROUND OF THE INVENTION

1. Field of the Invention

The invention relates to cosmetic compositions containing agglomerates with particular particle sizes.

2. The Prior Art

It is well known that inorganic particles such as e.g. oxides like iron oxides, titanium dioxide, zinc oxide etc. in cosmetic emulsions tend to form agglomerates of various sizes. Consequently, application of such emulsions to the skin can be disagreeable if large agglomerates first have to be dispersed by rubbing. The problem increases with diminishing particle size of the products applied. It is therefore often necessary to counteract such agglomerate formation with other additives.

From EP-B-406657, lamellar substrates are known comprising at least 0.5% wt spherical particles with a small-diameter of approx. 0.05 to 50 μm when compared to the lamellar substrates. A stated particular advantage of the invention is the occurrence of deagglomeration of the lamellar substrates as a result of the addition of spherical particles of e.g. $SiO_2$, $TiO_2$ and $ZrO_2$.

Furthermore, WO 96/17588 states that by adding $SiO_2$ to kaolin which also forms lamellar substrates, an increase in the kaolin content in cosmetic compositions is made possible.

EP-A-704502 describes the improvement of the protective effect of ZnO by dispersion in an alkali metal silicate solution gelled by the addition of $CO_2$, whereby $SiO_2$ containing ZnO is obtained.

SUMMARY OF THE INVENTION

It is thus the object of the present invention to develop cosmetic compositions with very good spreading characteristics on the skin, without the agglomeration of inorganic particles such as oxides having a disagreeable effect.

Surprisingly, it was found that the addition of spherical, non-porous $SiO_2$ particles of a particular particle size to other essentially spherical particles does not cause any deagglomeration, but results in defined agglomerates whose particle size is particularly advantageous for cosmetic preparations because these compositions allow very homogenous spreading on the skin, show very good reflection of UV radiation and in cosmetic sunscreen preparations with $TiO_2$ and/or ZnO achieve at least equal sunscreen factors as is the case with known sunscreen preparations, while achieving higher stability of the sunscreen factor (SPF).

The invention thus provides for the preparation of cosmetic compositions with agglomerated substrates comprising a content of spherical and porous $SiO_2$ particles, with the $SiO_2$ particles comprising a particle size ranging from 0.05 μm to 1.5 μm, where apart from the $SiO_2$ particles other inorganic particle-shaped materials of spherical structure are present, with the spherical $SiO_2$ particles forming defined agglomerates with other inorganic materials, with a particle size ranging from 0.06 μm to 5 μm. The proportion of agglomerates in the cosmetic composition ranges from 0.1 to 30% wt.

The agglomerated substrates are further characterised in that they are produced by mixing the spherical non-porous $SiO_2$ particles with the other inorganic particle-shaped materials of spherical structure present dry or as an oily dispersion with a viscosity of 13,500 to 200,000 cps, individually or mixed, maintaining a pH value of 5.5 to 7 such that part of the total water is to be added until a paste-like consistency is attained, with stirring for 20 to 100 minutes, with the remaining water subsequently being added while the pH value is maintained and homogenisation taking place at 3,000 to 5,000 rpm; with the temperature during the mixing processes ranging from 35 to 48° C. The dispersion obtained is then worked into the cosmetic composition in the usual manner with the proportion of agglomerates in the cosmetic composition being between 0.1 and 30% wt.

Of particular advantage is the use of highly monodispersed non-porous spherical $SiO_2$ particles according to DE3616133 produced by hydrolytic polycondensation of tetraalkoxysilane in an aqueous-alcoholic-ammoniacal medium, with a sol being produced from primary particles and subsequently the $SiO_2$ particles obtained being reduced to the desired particle size of approx. 0.05 to 10 μm by controlled adding, depending on the reaction process, of tetraalkoxysilane.

However, it is also possible to use $SiO_2$ particles produced according to other processes as far as they are non-porous and spherical, and comprise the respective particle size. If the use of $TiO_2$ in the composition is desired, particles may be used which comprise approx. 80% $SiO_2$ and 20% $TiO_2$.

The other inorganic particle-shaped materials of spherical structure used in the cosmetic composition according to the invention are mostly oxides such as iron oxides, e.g. $Fe_2O_3$, $Fe_3O_4$, FeO or mixed oxides; titanium dioxide; zinc oxide; zirconium dioxide; pigments; or magnetically hard single-grade particles (single-crystals) made of barium hexaferrite or strontium hexaferrite with a high corrective field intensity of 4,000 to 5,000 Oersted according to WO 95/03061.

Further pigments may for example be selected from among mica, kaolin, talcum, nylon globules, ceramic globules, expanded and non-expanded synthetic polymer powders, powdery natural organic compounds such as ground solid algae, encapsulated and non-encapsulated cereal starches as well as addition products comprising organic dyes.

In the context of the present invention, the term "inorganic spherical particles" denotes a round, spherical to at most ellipsoid shape of the particles.

The proportion of the agglomerates in the entire composition can range from 0.1 to 30% wt, preferably 0.5 to 25% wt.

Depending on the desired effect of the other inorganic particle-shaped materials, their ratio in respect of each other can vary widely. If e.g. in the case of sunscreen preparations, protection against UV-A radiation is emphasised, the ratio of $TiO_2$:ZnO can range from 1:1 to 1:10. By contrast, if the emphasis is on protection against UV-B radiation, the ratio of $TiO_2$:ZnO can range from 100:1 to 20:1.

The ratio $TiO_2$:$SiO_2$ or ZnO:$SiO_2$ can generally be between 100:1 and 1:1, preferably 20:1 to 2:1.

In a combination of $TiO_2$/ZnO/$SiO_2$, the ratio $TiO_2$:ZnO:$SiO_2$ can range from 1:100:1 to 100:1:1.

The ratio of other inorganic particle-shaped materials to $SiO_2$ can be between 100:1 to 1:1.

Apart from the agglomerates defined according to the invention, the composition may comprise usual cosmetic adjuvants or active substances in a proportion from 99.9 to 70% wt.

Cosmetic active-ingredients include e.g. emulsifiers, inorganic and organic sunscreen agents, radical interceptors, moisturisers, vitamins, enzymes, active vegetable substances, polymers, melanin, antioxidants, natural anti-inflammatory substances, oxygen-laden asymmetric lamellar aggregates according to WO 94/00109; digestion products of yeasts or vegetable substances made by a gentle ultrasonic digestion process according to WO 94/13783, kaolin as well as kaolin modified by $SiO_2$ according to WO 94/17588.

Cosmetic adjuvants include water, various vegetable oils, mineral oil, silicon oil, gelatinising agents, dyes, preservatives, perfume, monovalent and polyvalent alcohols, protectants, pH regulators, waxes etc.

In the case of cosmetic preparations according to the invention, comprising $TiO_2$ and/or ZnO, sunscreen factors are obtained which with the same content of active substances are at least equivalent to those known from conventional sunscreen preparations, e.g. from EP-B-433086 which describes a synergistic $TiO_2$/ZnO combination claiming $TiO_2$ of less than 35 nm and ZnO of less than 50 nm, optionally containing $TiO_2$ at 2 to 25% wt. With 24.5% $TiO_2$ and 10% ZnO, the sunscreen factor according to Cole and VanFossen should have a value of 32 and the composition should have an aesthetic appearance.

However, with a sunscreen protection factor which is at lest equivalent, the sunscreen preparations according to the invention provide a better stability of the sunscreen factor, i.e. the effect is longer lasting. This has been proven beyond doubt in several trials. The composition according to the invention also has a reduced whitening effect when compared to other known compositions.

The cosmetic composition with agglomerated substrates can be an O/W emulsion, W/O emulsion, multiple emulsion (O/W/O or W/O/W) or a gel. Various application forms can be produced, such as cremes, lotions, gels, make-ups, lipsticks, powders, masks, sprays, all types of sunscreen preparations, pre-tanning preparations, wax-like products etc.

The invention also relates to the production of the cosmetic composition with agglomerated substrates. Production is by mixing spherical non-porous $SiO_2$ particles with other inorganic particle-shaped materials of spherical structure present dry or as an oily dispersion with a viscosity of 13,500 to 200,000 cps, individually or mixed, maintaining a pH value of 5.5 to 7 such that part of the total water is to be added until a paste-like consistency is attained, with stirring for 20 to 100 minutes, with the remaining water subsequently being added while the pH value is maintained and homogenisation taking place at 3,000 to 5,000 rpm for 20 to 60 min.; with the temperature during the mixing processes ranging from 35 to 48° C. The spherical $SiO_2$ forms defined agglomerates with the other inorganic materials, with a particle size ranging from 0.06 µm to 5 µm. The dispersion obtained is then worked into the cosmetic composition in the usual manner with the proportion of agglomerates in the cosmetic composition being between 0.1 and 30% wt.

If the other inorganic materials are present in the usual powdery form it is advantageous to carry out mixing with the $SiO_2$ particles at 35 to 45° C., and at less than 200 rpm for 3 to 20 minutes.

If dispersions of the other inorganic materials are already present, they are to be mixed with the particle-shaped $SiO_2$ at 35 to 45° C. at less than 200 rpm for 40 to 100 minutes, with water to be added depending on the desired concentration, and with subsequent homogenisation taking place.

When e.g. $TiO_2$ is prepared, the use of oily dispersions with viscosities of 13,500 to 200,000 cps is advantageous, with the respective pulverising processes taking place prior to mixing-in the $SiO_2$.

When e.g. ZnO is prepared, the use of oily dispersions or dispersions containing wax, with viscosities of 20,000 to 50,000 cps is advantageous, with the respective pulverising processes taking place prior to mixing-in the ZnO.

It is possible to produce mixtures of individual other inorganic materials with the spherical $SiO_2$ and then to introduce them into the cosmetic formulation one after the other. But it is also possible to produce finished mixtures of several other inorganic materials, e.g. $TiO_2$/ZnO/$SiO_2$ and then add them to the cosmetic formulation.

For agglomerate formation care must be taken that the initial stirring when introducing the $SiO_2$ e.g. into a $TiO_2$ dispersion, takes place very slowly, e.g. at 300–400 rpm and at temperatures between 35 and 42° C., that subsequently homogenisation takes place and that finally the second dispersion (e.g. ZnO) is also introduced with slow stirring at temperatures of 40 to 48° C., and that only then does homogenisation take place once more.

Suitable homogenisation conditions are e.g. 3,000 to 5,000 rpm.

The pH value must be maintained during the entire mixing process; it can be controlled e.g. via added buffer solutions such as phosphate buffers.

If solid cosmetic compositions such as pressed powders are made, no water is added but instead, a binder is added to the dry mixture which is usually oil based, comprising several components.

The compositions according to the invention, e.g. comprising iron oxides, are eminently suitable for decorative cosmetics, e.g. for make up, lipsticks, coloration cremes etc.

DETAILED DESCRIPTION OF PREFERRED EMBODIMENTS

Below, the invention is explained in more detail by means of examples. All percentage references relate to weight (mass) unless otherwise stated.

EXAMPLE 1

Production of an Agglomerate Dispersion

Monodispersed, non-porous, spherical $SiO_2$ (Merck) with a particle size of 0.1 µm at a ratio of 1:30 was intermixed with dry spherical $TiO_2$ at 35–36° C. for 8 minutes at 140 rpm. Subsequently, water was added and stirring took place at 320 rpm for 30 minutes until a paste-like consistency was obtained. Additional water was then added to the mixture and homogenisation took place at 3800 rpm for 20 minutes, resulting in a dispersion with a viscosity of approx. 23,000 cps. During this time the pH value was approx. 6. The agglomerates had a medium particle size of 0.95 µm, measured with a master sizer (Malvern Instruments Ltd., Worcs., Great Britain).

In the same way and under similar conditions, dispersions containing ZnO and $Fe_2O_3$ were produced.

EXAMPLE 2

Liquid Makeup (SPF15)

Phase A

| | |
|---|---|
| Carnation oil | 19% |
| Silicon oil | 10% |
| Jojoba oil | 5% |
| Magnesium stearate | 2% |

Phase B

| | |
|---|---|
| Water | q.s. ad 100 |
| Magnesium sulphate | 0.9% |
| Dye | 4% |
| Kaolin modified with $SiO_2$ according to WO 96/17588 | 2.5% |
| $TiO_2/SiO_2$ according to the invention (ratio 4:1) | 5.0% |
| $ZnO/SiO_2$ according to the invention (ratio 1:1) | 2.0% |

Phase C

| | |
|---|---|
| Pholosine complex according to DE patent application 19654508.0 Comprising: | 2.0% |
| Laminaria saccharina extract | 40% |
| Lilium candidum extract | 45% |
| Glycyrrhetinic acid | 10% |
| Matricaria recutita extract | 5% |

Phase D

| | |
|---|---|
| Asymmetric lamellar aggregates with 2% magnetically hard single-grade particles according to WO 95/03061 | 1.0% |
| Palm oil | 0.5% |

The ingredients of phases A and B were stirred separately, at approx. 55° C. The aggregate dispersions containing $TiO_2$ and ZnO according to the invention were produced according to the procedure described in example 1 with corresponding starting quantities. Subsequently, the phases A and B were placed together, homogenised well and cooled to 40° C. Then phases C and D were added. A water-resistant liquid makeup with very good skin sensation, even application ability and long-lasting appearance was obtained. The skin protection factor (SPF) was very well stabilised.

EXAMPLE 2

O/W Emulsion (SPF50)

Phase A

| | |
|---|---|
| Glyceryl stearate/PEG 100 stearate | 4.5% |
| Cetearyl alcohol | 2.0% |
| Isohexadecane | 1.5% |

Phase B

| | |
|---|---|
| Water | q.s. ad 100 |
| Glycerine | 2.0% |
| $TiO_2/SiO_2$ according to the invention (ratio 70:30) | 25% |
| $ZnO/SiO_2$ according to the invention (ratio 3:1) | 5% |
| Kaolin modified with $SiO_2$ according to WO 96/17588 | 3.0% |
| Carbomer | 0.1% |

Phase C

Triethanolamine 0.1%

Phase D

| | |
|---|---|
| Silicon oil | 2.0% |
| Babassu oil | 1.5% |
| Preservative | 0.5% |

Phase E

| | |
|---|---|
| Baker's yeast digestion product according to WO 94/13783 | 0.5% |
| Asymmetric lamellar aggregate of phospholipids, loaded to saturation level with oxygen, containing 30% phospatidyl choline and perfluorodecaline according to WO 94/00109 | 2.5% |
| Palm oil | 0.5% |

Phases A and B were separated by mixing the individual components, with aggregates containing $SiO_2$ having been prepared according to example 1 at approx. 55° C.

Subsequently both phases were mixed and homogenised. After cooling to approx. 40° C., phase C was added as were phases D and E which had also been produced separately. The well homogenised O/W emulsion obtained had a very stable and high sunscreen factor, was able to be applied very evenly and homogeneously on the skin and was very long-lasting.

EXAMPLE 3

Sunscreen Powder with UV-A/UV-B Protection (SPF 20)

| | |
|---|---|
| Kaolin modified with $SiO_2$ according to WO 96/17588 | 10% |
| Standard kaolin | 5% |
| Talcum | q.s. ad 100 |
| Dye | 4.0% |
| $TiO_2/SiO_2$ according to the invention (ratio 50:50) | 7% |
| $ZnO/SiO_2$ according to the invention (ratio 70:30) | 3% |
| $Fe_2O_3/SiO_2$ according to the invention (ratio 60:40) | 3% |

The other inorganic spherical particles $TiO_2$, ZnO and $Fe_2O_3$, which had been mixed separately, were mixed at room temperature with the talcum, kaolin and the dye. Then followed the addition of a binder for the pressed powder. The binder comprised jojoba oil, babassu oil and silicon oil.

What is claimed is:

1. Sunscreen composition containing agglomerated substrates, comprising a content of spherical, non-porous $SiO_2$ particles with a particle size ranging from 0.05 to 1.5 µm, and a content of other inorganic particle-shaped materials of spherical structure;

wherein said other inorganic particle-shaped materials are zinc oxide and titanium dioxide;

with the spherical $SiO_2$ forming defined agglomerates with the other inorganic materials, of a particle size ranging from 0.06 µm to 5 µm and with the proportion of agglomerates in the sunscreen composition ranging from 0.1 to 30% wt;

produced by mixing the spherical non-porous $SiO_2$ particles with the other inorganic particle-shaped materials of spherical structure present dry or as an oily dispersion with a viscosity of 13,500 to 200,000 cps, wherein said other inorganic particle-shaped materials are zinc oxide and titanium dioxide;

individually or mixed, maintaining a pH value of 5.5 to 7 such that part of the total water is to be added until a paste-like consistency is attained, with stirring for 20 to 100 minutes, with the remaining water subsequently being added while the pH value is maintained and homogenisation taking place at 3,000 to 5,000 rpm; with the temperature during the mixing processes ranging from 35 to 48° C., and with the dispersion obtained being worked into the sunscreen composition in the usual manner with the proportion of agglomerates in the sunscreen composition being between 0.1 and 30% wt.

2. A composition according to claim 1, wherein the proportion of the other inorganic particle-shaped materials to the spherical $SiO_2$ ranges from 100:1 to more than 1:1.

3. Composition according to claim 1 wherein they are a creme, lotion, sunscreen preparation, lipstick, make-up, mask or gel.

4. Composition according to claim 1, wherein in sunscreen preparations with improved UV-A protection the proportion of zinc oxide to titanium dioxide ranges from 1:1 to 10:1.

5. Composition according to claim 1, wherein in sunscreen preparations with improved UV-B protection the proportion of zinc oxide to titanium dioxide ranges from 1:20 to 1:100.

6. Composition according to claim 1 wherein the proportion of agglomerates in the sunscreen composition ranges from 0.5 to 25% wt.

7. A process for producing sunscreen compositions with agglomerated substrates, comprising intermixing of spherical non-porous $SiO_2$ particles with a particle size ranging from 0.05 to 1.5 µm, with other inorganic particle-shaped materials of spherical structure, wherein said other inorganic particle-shaped materials are zinc oxide and titanium dioxide;

to obtain defined agglomerates of a particle size of 0.06 µm to 5 µm, with the other inorganic particle-shaped materials with spherical structure which are present dry or as an oily dispersion with a viscosity of 13,500 to 200,000 cps being mixed together individually or as a mixture with the spherical non-porous $SiO_2$ particles while maintaining a pH value of 5.5 to 7 such that part of the total water is to be added until a paste-like consistency is attained, with stirring for 20 to 100 minutes, with the remaining water subsequently being added while the pH value is maintained and homogenisation taking place for 20 to 60 minutes;

with the temperature during the mixing processes ranging from 35 to 48° C., and with the dispersion obtained being worked into the sunscreen composition in the usual manner with the proportion of agglomerates in the sunscreen composition being between 0.1 and 30% wt.

8. A process according to claim 7 wherein in dry sunscreen composition an oily binder is added instead of water.

9. A process according to claim 7, wherein stirring takes place at 300 to 400 rpm.

10. A process according to claim 7, wherein homogenisation takes place at 3,000 to 5,000 rpm.

11. A composition according to claim 2, wherein the proportion of the other inorganic particle-shaped materials to the spherical $SiO_2$ ranges from 20:1 to 2:1.

* * * * *